US008213467B2

(12) United States Patent  
Little et al.

(10) Patent No.: US 8,213,467 B2
(45) Date of Patent: Jul. 3, 2012

(54) SYSTEMS AND METHODS PROVIDING ASICS FOR USE IN MULTIPLE APPLICATIONS

(75) Inventors: Blake W. Little, Bothell, WA (US); Ramachandra Pailoor, Woodinville, WA (US)

(73) Assignee: SonoSite, Inc., Bothell, WA (US)

( * ) Notice: Subject to any disclaimer, the term of this patent is extended or adjusted under 35 U.S.C. 154(b) by 2492 days.

(21) Appl. No.: 10/821,123

(22) Filed: Apr. 8, 2004

(65) Prior Publication Data

US 2005/0228287 A1 Oct. 13, 2005

(51) Int. Cl.
 H04J 3/02 (2006.01)
(52) U.S. Cl. .......................... 370/537; 600/444; 600/447
(58) Field of Classification Search .................. 600/437, 600/441, 446, 459, 440, 444, 445, 447
See application file for complete search history.

(56) References Cited

U.S. PATENT DOCUMENTS

| | | | | |
|---|---|---|---|---|
| 5,000,052 A | * | 3/1991 | Sipin ......................... 73/863.03 |
| 5,177,697 A | * | 1/1993 | Schanen et al. ................. 702/87 |
| 5,520,187 A | * | 5/1996 | Snyder .......................... 600/459 |
| 5,524,629 A | * | 6/1996 | Mahony ........................ 600/454 |
| 5,777,763 A | * | 7/1998 | Tomlinson, III ............... 398/87 |
| 5,817,024 A | * | 10/1998 | Ogle et al. ..................... 600/447 |
| 5,893,363 A | * | 4/1999 | Little et al. ..................... 600/447 |
| 6,004,631 A | | 12/1999 | Mori |
| 6,102,863 A | * | 8/2000 | Pflugrath et al. .............. 600/447 |
| 6,126,602 A | * | 10/2000 | Savord et al. .................. 600/447 |
| 6,203,498 B1 | * | 3/2001 | Bunce et al. ................... 600/446 |
| 6,333,648 B1 | * | 12/2001 | Tumer ............................ 327/70 |
| 6,383,139 B1 | * | 5/2002 | Hwang et al. ................. 600/441 |
| 6,468,213 B1 | * | 10/2002 | Knell et al. .................... 600/437 |
| 6,491,634 B1 | * | 12/2002 | Leavitt et al. ................. 600/447 |
| 6,695,783 B2 | * | 2/2004 | Henderson et al. ........... 600/443 |
| 6,783,493 B2 | * | 8/2004 | Chiang et al. ................. 600/437 |
| 7,169,108 B2 | * | 1/2007 | Little et al. .................... 600/457 |
| 7,257,609 B1 | * | 8/2007 | Kosunen et al. .............. 708/493 |
| 2002/0082500 A1 | * | 6/2002 | Henderson et al. ........... 600/443 |
| 2003/0176787 A1 | * | 9/2003 | Gilbert et al. ................. 600/437 |
| 2003/0185205 A1 | * | 10/2003 | Beshai .......................... 370/370 |
| 2004/0015079 A1 | * | 1/2004 | Berger et al. ................. 600/437 |
| 2004/0239377 A1 | * | 12/2004 | Tumer et al. ................... 327/94 |
| 2005/0113698 A1 | * | 5/2005 | Kristoffersen et al. ....... 600/459 |
| 2005/0113699 A1 | * | 5/2005 | Haugen et al. ................ 600/459 |
| 2005/0124890 A1 | * | 6/2005 | Halmann et al. .............. 600/446 |
| 2005/0203402 A1 | * | 9/2005 | Angelsen et al. ............. 600/447 |
| 2005/0228287 A1 | * | 10/2005 | Little et al. .................... 600/459 |
| 2005/0265267 A1 | * | 12/2005 | Hwang .......................... 370/310 |
| 2007/0071266 A1 | * | 3/2007 | Little et al. .................... 381/328 |
| 2007/0239001 A1 | * | 10/2007 | Mehi et al. .................... 600/437 |

FOREIGN PATENT DOCUMENTS

KR 10-375080 9/1996
WO WO 2004003962 A2 1/2004

OTHER PUBLICATIONS

Weste N.H.: "CMOS VLSI Design: a circuits and systems perspective" 1993, Addison/Wesley, p. 19, XP002350734.
Anonymous: "Multiplexed Data Acquisition System Considerations" Intersil Application Notes, Aug. 2002, pp. 1-3, XP002350732.
Partial International Search Report issued for PCT/US2005/012109 dated Nov. 14, 2005.

* cited by examiner

*Primary Examiner* — Phuc Tran
(74) *Attorney, Agent, or Firm* — Fenwick & West LLP (57) ABSTRACT

A system comprises an application specific integrated circuit (ASIC) adapted for use in a plurality of circuit configurations. The circuit configurations provide for different numbers of signal channels for further processing using same circuitry of said application specific integrated circuit.

19 Claims, 4 Drawing Sheets

SYSTEMS AND METHODS PROVIDING ASICS FOR USE IN MULTIPLE APPLICATIONS

TECHNICAL FIELD

The embodiments disclosed herein relate in general to ASICs adapted for use in multiple system configurations.

BACKGROUND OF THE INVENTION

Sonogram systems may use a variety of systems and methods to create images of internal body parts for viewing. Basic sonogram systems usually employ a transducer array, made up of a number of transducer elements, coupled to an ultrasound system. The function of the transducer array and system are to create an acoustic beam (a beam of sound waves) to penetrate the human body and then to receive sound waves as they are reflected back to the transducer array from tissues and organs. The reflection of the sound waves may be processed to produce a visual image representing the internal structures of the human body. Sonography, or the use of sonograms for diagnosis, is often employed as a non-invasive way to view fetal growth or to view internal injuries.

Often the area to be imaged is conceptually divided into long, thin strips, called lines. A sonogram machine may then focus an acoustic beam on each line to provide an image of the whole area. The group of lines that make up the image area are referred to as a "frame." Similarly, during further processing, signal processing equipment, possibly including functions such as digital filters and digital scan conversion, may construct a viewable image from a frame, arranging and filtering the data from the lines in the frame into signals, which when provided to a display, present to a human viewer a visual representation of the area. Real-time imaging may then be provided by, for example, repeating the frames. Application Specific Integrated Circuits (ASICs) can be used to perform various functions in the aforementioned ultrasound image acquisitions and processing. For example, various transmit and/or receive circuits (such as may include amplifiers, filters, multiplexors, summers, etc.), beam formers (which control the ultra-sonic pulses to create beams by a transducer array), and like signal processing circuitry may be implemented in ASICs.

An ASIC is a chip developed for employment in a specific system, rather than a general-purpose chip, such as a digital signal processor or a microprocessor. ASICs may be inexpensive to produce once designed and may allow for a smaller chip to perform a particular task in a shorter amount of time. ASICs are usually "hardwired" to perform a specific function, which means that they are less flexible than a Field Programmable Gate Array (FPGA), which may be programmed to perform a specific function by a user in the "field" or a general purpose integrated circuit, such as a CPU. Because ASICs are applications-specific, they are typically not well-suited for use in a number of different system configurations. For example, multiple sonogram systems (even systems from a common manufacturer), such as may provide different levels of image quality or image processing, are often not able to use the same ASICs. Instead, each system must generally employ a unique chip set. Further, traditional sonogram systems that employ ASICs are typically not readily able to accommodate added features after such systems have been manufactured because of the lack of flexibility offered by ASICs. Thus, an old system is not able to be reprogrammed to perform a new mode of operation without significant hardware replacement.

BRIEF SUMMARY OF THE INVENTION

According to at least one embodiment, a system comprises an application specific integrated circuit (ASIC) adapted for use in a plurality of circuit configurations, said circuit configurations providing for different numbers of signal channels for further processing, using the same circuitry of said application specific integrated circuit.

According to at least one other embodiment, a method comprises determining a number of channels for use in a data path, and configuring an ASIC adapted for use in a plurality of configurations to provide said determined number of channels.

Additionally, according to at least one other embodiment, an apparatus comprises a sonogram imaging system including a transducer, a beam former, a data path including a plurality of information channels connecting the transducer to the beam former, and an ASIC in communication with the data path between the transducer and the beam former, including circuitry operable as a bank of multiplexors or as a summer/cross-point switch, wherein the ASIC is adapted for use in a plurality of circuit configurations employing different numbers of information channels.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Figure 1:
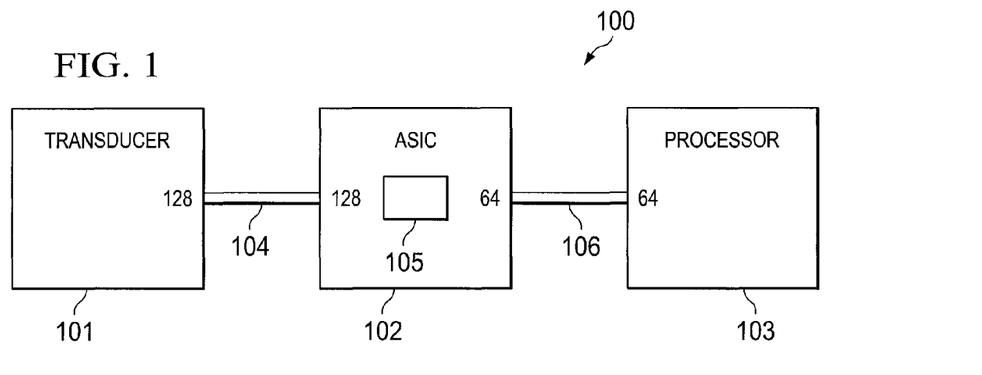
FIG. 1 is an illustration of an exemplary system, adapted according to various embodiments, employing an ASIC for use in multiple system configurations.

FIG. 1 is an illustration of exemplary system 100, adapted according to various embodiments, employing an ASIC for use in multiple system configurations. Transducer 101 is connected to ASIC 102 via data path 104. Similarly, ASIC 102 is connected to control/processing circuit 103 via data path 106. Control/processing circuitry 103 may comprise a beam former, an analog to digital converter, a CPU and other components which may be found in a sonogram imaging system. Transducer 101, in this embodiment, is an array of transducer elements (not shown), and therefore, has a number of bidirectional inputs/outputs that are serviced by a number of signal channels (not shown) in data path 104. The signal channels provide electrical communication among transducer 101, ASIC 102, and control/processing circuit 103. Control/processing circuit 103, in this example, provides control to the components of system 100, including ASIC 102 and transducer 101, and also provides some signal processing to received signals. Transducer 101 communicates with ASIC 102 and with control/processing circuit 103. In this example embodiment, transducer 101 has one hundred twenty-eight transducer elements, and each of those elements has an input/output. None of the input/outputs are combined before they enter data path 104, such that data path 104 provides one hundred twenty-eight signal channels from transducer 101 to ASIC 102.

ASIC 102 includes circuitry 105, which is adapted for use in a variety of systems, each employing a different number of signal channels between transducer 101 and control/processing circuit 103. In some embodiments, system 101 does not provide support for all one hundred twenty-eight transducer elements, and thus, is a lower-processing-power and lower-power-consumption system than a system that does provide output information for all one hundred twenty-eight elements. In an example embodiment, ASIC 102 receives one hundred twenty-eight channels on data path 104 and reduces by a factor of two the number of signal channels to be fed to data path 106, thereby providing control/processing circuit 103 with sixty-four signal channels of information from transducer 101. In a first configuration, circuitry 105 in ASIC 102 may define a number of signal channels by acting as a bank of 2:1 multiplexors, thereby passing signals from only one of every two channels at any given time. In other example embodiments of the first configuration, circuitry 105 may allow ASIC 102 to act as a bank of 4:1 multiplexors. In example embodiment of a second configuration, circuitry 105 may provide a summing functionality, thereby treating one hundred twenty-eight channels as sixty-four pairs, each pair to be summed into one output, such that sixty-four summed outputs are produced. In example embodiments of the second configuration, ASIC 102 may employ circuitry 105 to act as a cross-point switch to route signal channels to control circuit 103, such that it does not decrease a number of channels at all, but rather may maintain a number of channels, or in some embodiments may even route some channels to multiple components (not shown) thereby increasing the total number of output channels.

Thus, in embodiments of both of the foregoing configurations, ASIC 102 contains circuitry 105, which allows ASIC 102 to be adapted for use in many systems, even though such systems may each employ a different number of signal channels. Further, ASIC 102 can be used in various combinations, such as in parallel or in series with other ASICs. Some combinations may employ multiple ASICs 102 in series or cascaded to scale a system for an appropriate use. Still other combinations may employ multiple ASICs with different circuitry 105 to provide desired functionality. While multiplexing, summing, and cross-point switching have been named as methods to define a number of channels, any method to define the number of channels by ASIC 102 is within the scope of the invention, including all methods now known or later developed.

Figure 2A:
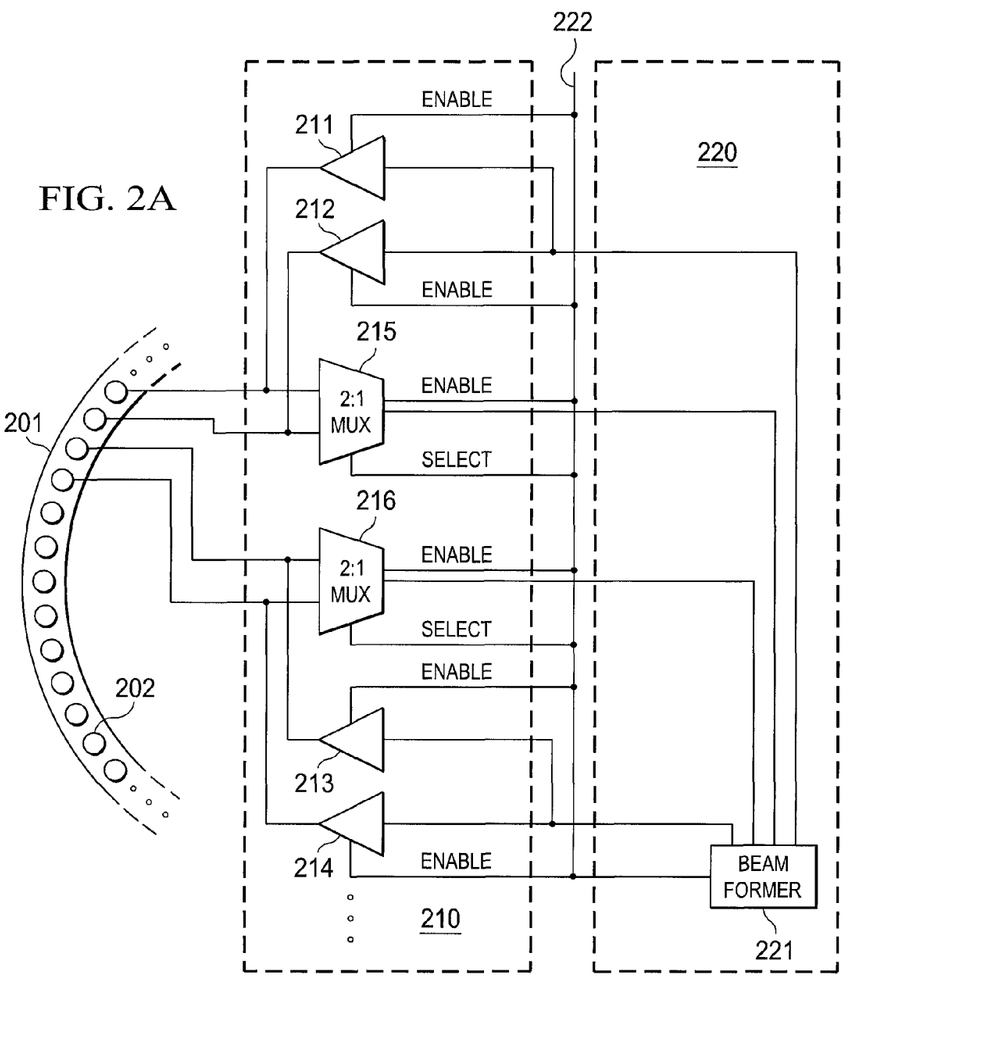
FIGS. 2A and 2B are illustrations of an exemplary system, adapted according to various embodiments, employing an ASIC adapted for use in multiple system configurations.
Figure 2B:
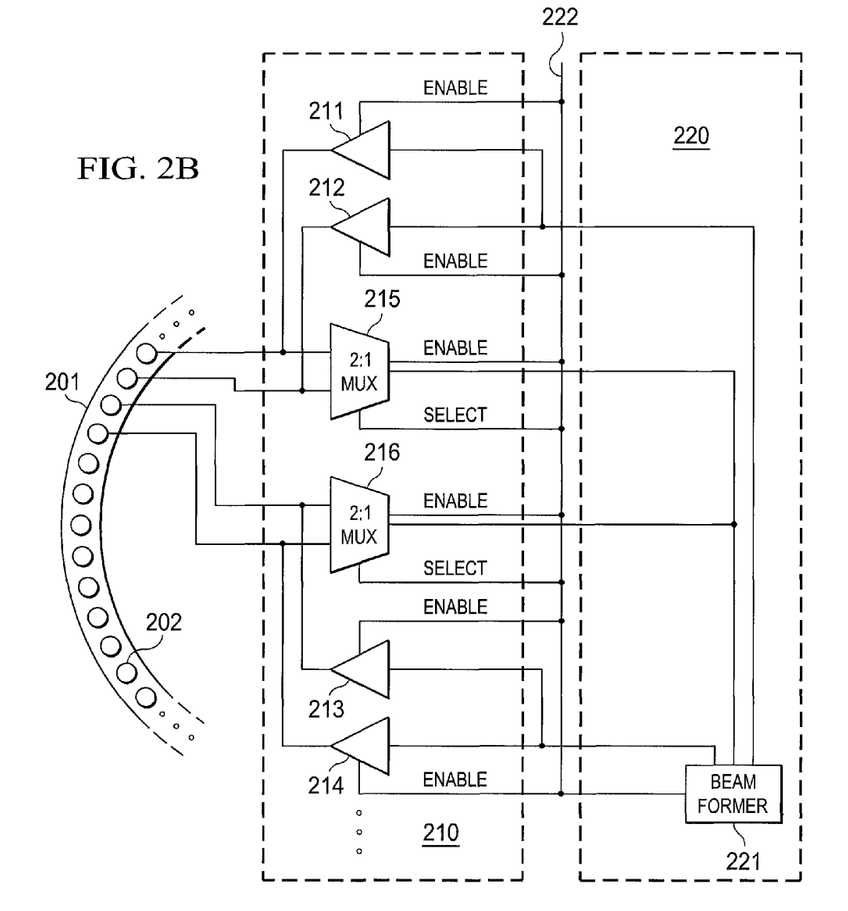

FIGS. 2A and 2B are illustrations of exemplary system 200, adapted according to various embodiments, employing ASIC 210 adapted for use in multiple system configurations. In this particular embodiment, ASIC 210 is operable to reduce a number of signal channels along a data path, both to and from transducer 201 and additional ultrasound processing equipment 220.

Specifically, FIG. 2A is a schematic diagram of a portion of a diagnostic sonogram machine according to various embodiments. System 200 includes transducer 201, which utilizes a number of transducer elements, represented as circles 202 within transducer 201. System 200 also includes ASIC 210, and additional ultrasound processing equipment 220, which may include, among other things, control/processing circuitry (in this case, beam former 221) and processing and display equipment (not shown). As will be explained in more detail later, ASIC 210, in this embodiment, operates to supply transducer 201 with high-power pulses to produce a sonic beam for use in diagnostic sonography and operates to reduce a number of signal channels for transducer 201.

ASIC 210 includes circuitry within to define a number of signal channels in communication with transducer 201. ASIC 210 includes, among other things, multiplexors 215 and 216 and amplifiers 211-214. Any number of multiplexors and amplifiers is within the scope of the invention, as two multiplexors and four amplifiers are for simplicity of illustration only. Multiplexor (mux) 215, amplifiers 211 and 212, and the signal paths connecting those components acts as a transmit/receive switch, as explained below. Similarly, mux 216, amplifiers 213 and 214, and the wiring connecting those components act as another transmit/receive switch.

Transmit and receive operations are now discussed with regard to the transmit/receive switch formed by mux 215 and amplifiers 211 and 212; however, it should be noted that the transmit/receive switch formed by mux 216 and amplifiers 213 and 214 operates in a similar manner. During a transmit operation, beam former 221, included in additional ultrasound processing equipment 220, sends a low-energy pulse to amplifiers 211 and 212, which operate to increase the energy of the pulse to produce a beam using a combination of the elements in transducer 201, including at least one of the elements coupled to amplifiers 211 and 212 of the example. During the transmit operation, the enable switches on one or more of amplifiers 211 and 212 are stimulated by beam former 221, thereby allowing the pulse to pass into transducer 201, thereby producing a desired beam. In any given transmit operation, one or both amplifier enable switches may be stimulated, depending on the desired beam. Also, during the transmit operation, the enable switch on mux 215 is preferably not stimulated, such that no current flows through mux 215. Thus, by enabling one or more of amplifiers 211 and 212 and disabling mux 215, a high-energy signal may be sent to transducer 201 while preventing the high-energy signal from passing though mux 215 to the receive circuitry of the additional ultrasound processing equipment 220. The enable lines can be used to accommodate a number of different signal splitting configurations. The switching function is important because transmit signals, in this embodiment, are higher-power signals than are receive signals, such that a transmit signal may damage circuitry in other components if allowed to flow through mux 215. Of course, the receive switch functionality may be omitted according to embodiments, if desired.

This particular embodiment of ASIC 210 facilitates a reduction of the number of transmit channels by allowing a branching of one transmit channel from additional ultrasound processing equipment 220 into two channels, while still allowing separate enabling of each channel. Other embodiments may use different branching configurations, such as 1:1 or 3:1. The depicted embodiment still allows a large degree of control of transmit operations by providing enable switches on amplifiers 211-214 to facilitate beam forming.

During a receive operation, mux 215 is enabled by beam former 221, and amplifiers 211 and 212 are disabled (in some embodiments, to conserve power), thereby allowing current to flow from transducer 201 through mux 215 and to additional ultrasound processing equipment 220. In this example embodiment, muxes 215 and 216 are 2:1 muxes, meaning that while two signals are input to each mux, only one signal is output from each mux. Accordingly, if a 2:1 mux is placed at every two transducer elements, at any given time, only signals from half of the elements are passed to additional ultrasound processing equipment 220. By employing muxes, such as muxes 215 and 216, system 200 may reduce by a factor of two the number of receive signal channels that it utilizes. Muxes, such as 215 and 216 may operate, for example, by receiving a signal on a select line, which instructs such mux to pass a selected one of the two signals. Thus, this embodiment decreases the number of signal channels by a factor of two. Muxes 215 and 216 are adapted for use in other configurations, as explained below.

Such embodiments that reduce a number of transmit or receive channels provides to a system compatibility with a transducer that has elements in excess the number of bi-directional input/outputs. Further, such embodiments may reduce the amount of power consumption and processing needed by the system, thereby facilitating design of lower-cost or portable systems.

FIG. 2B is a schematic diagram of a portion of a diagnostic sonogram machine according to various embodiments. As explained earlier, muxes 215 and 216 include enable switches. By selectively enabling one of muxes 215 and 216 during a receive operation, 2:1 muxes 215 and 216 act together as a 4:1 mux, such that during a receive operation, signals from only one out of every four transducer elements are received by additional ultrasound processing equipment 220. In such an embodiment, the outputs of muxes 215 and 216 may be tied together to provide one output for the pair. Such tying may be outside ASIC 210, such as by hardwiring connections between pins, or such tying may be inside ASIC 210, such as through a PROM-style burning process. Pairing up 2:1 muxes to form 4:1 muxes allows a system to reduce by a factor of four the number of signal channels. Further, alternative embodiments may group together more than two 2:1 muxes, such as four or eight, to provide 8:1 or 16:1 mux functionality, respectively. Thus, in this embodiment, ASIC 210 acts to reduce the number of signal channels in communication with additional ultrasound processing equipment 220 by a factor of four. As explained earlier, such reduction may reduce resolution or frame rate (the number of frames that may be completed in a unit of time) that may be provided by a system, such as system 200, but may also result in lower cost and decreased power consumption. Because ASIC 210 may facilitate connections between a transducer and other processing equipment when a variety of different numbers of signal channels are used, ASIC 210 is adapted for use in a variety of systems. Such adaptation may be useful to a manufacturer who produces several imaging systems and may want to utilize as few chip sets as possible in the manufacture of the several imaging systems.

In the embodiments depicted in FIGS. 2A and 2B, control for the select and enable switches is provided by beam former 221, in additional ultrasound processing equipment 220, as mentioned above. The control of the enable and select switches, in this example, is facilitated by digital bus 222, which may include a digital serial control bus, or any other structure operable to supply stimulation to such switches.

Figure 3A:
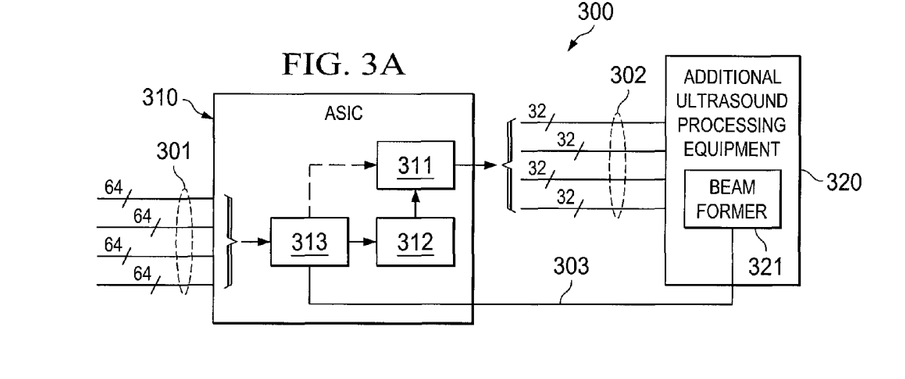
FIG. 3A is an illustration of an exemplary system, adapted according to various embodiments, employing an ASIC adapted for use in multiple system configurations and for performing summing operations.

FIG. 3A is an illustration of exemplary system 300, adapted according to various embodiments, employing ASIC 310 adapted for use in multiple system configurations and for performing summing operations. In this example embodiment, only receive operations will be the focus of this discussion of summing. A transducer (not shown) converts reflections of acoustic beams into electrical impulses, which are output, in some embodiments to an ASIC (not shown) to decreases a number of receive signal channels through, for example, muxes. The impulses are then output by that ASIC (not shown), in this example, on sixty-four receive signal channels 301 to ASIC 310. ASIC 310 includes logic 313, summing circuitry 312, and cross-point switch circuitry 311. Logic 313 receives, via bus 303, instructions from beam former 311 to perform summing on the signal channels. In this case, logic 313 instructs the data on the signal channels to be routed to and processed by circuitry 312 and 311 (notice the path to 311 that bypasses circuitry 312 is not used). A summing process operates, in this example, to pair up each of the sixty-four signal channels into one of thirty-two pairs. Each of the channels in each pair are then summed, and the resulting thirty-two sums are then routed (by circuitry 311) as thirty-two receive channels 302 to additional ultrasound processing equipment 320. Thus, in a summing mode, ASIC 310 may operate to decrease a number of signal channels, as in this example.

Such summing of signals may be accomplished, for example, through summing symmetrical signals. In a symmetric summing operation, ASIC 310 receives, in each pair, two signals that are very similar in their delay and weight due to their symmetry about an axis of the aperture provided by a transducer. Two signals may have the same delay when, for example, the path of the sonic beam through the transducer lens and the medium is substantially similar. Two signals may have the same weight when, for example, an algorithm that pieces the signals into a user display is programmed to apply substantially similar weight to such signals when processing an image from multiple signals. Because the delay and weight of each of the signals is substantially similar, those signals may be combined without causing incorrect phase-shifting and without attaching an incorrect weight to the information on the signals. Thus, when a processor transforms the signals from the transducer into a display for a user, the display not be affected adversely by phase-shifting or incorrect weighting. Symmetric summing also allows for preserving an aperture gain and frame rate even though the number of signal channels has been reduced. Symmetric summing, may, therefore, facilitate the creation of lower-power-consumption and lower-processing-power systems.

While the embodiment in FIG. 3A depicts sixty-four inputs and thirty-two output channels for ASIC 310, it should be noted that in other embodiments, ASICs, such as 310 may have more or fewer input and output channels. Further, in many practical summing embodiments, the signals that pair up symmetrically will change with each line to be formed. Thus, summing circuitry, such as circuitry 312, will usually not be hardwired to always sum any particular two signals, but will usually employ cross-point switch functionality to pair up and sum any two signals that are determined to be symmetric. Such determination of symmetry, in this example, is accomplished by beam former 321, which determines, based upon the beams formed, which channels contain symmetrical signals. Accordingly, beam former 321 then sends control signals to logic 313, via digital bus 303, to instruct circuitry 311 to pair up appropriate data signals. Thus, symmetrical summing may be a dynamic operation, changing for each line formed.

Additionally, another use of summing functionality, in some embodiments, is to combine signals channels servicing adjacent transducer elements, therefore, effectively constructing a larger transducer element for a beam former, such as beam former 321 to act on. This can be used with summing of symmetric elements as well to further reduce the beam former signal channel count. Adjacent summing may allow a scanhead (transducer) with a high element density (or fine pitch) to be used on a higher-end system that has large numbers of channels and also to be used on a lower-end system with fewer channels while maintaining an adequate frame rate.

It should be noted that though circuitry 312 is depicted as on a data path before circuitry 311, such depiction is purely for simplicity, and that such circuitry 311 and 312 works in concert in summing operations, such that data may be added in correct pairs and routed over correct channels to additional ultrasound processing equipment 320. Further, though logic 313 is depicted as being in the data path, such representation is also for simplicity, as other embodiments may employ similar logic outside of a data path, with that logic controlling the routing and processing of data in a like manner.

Figure 3B:
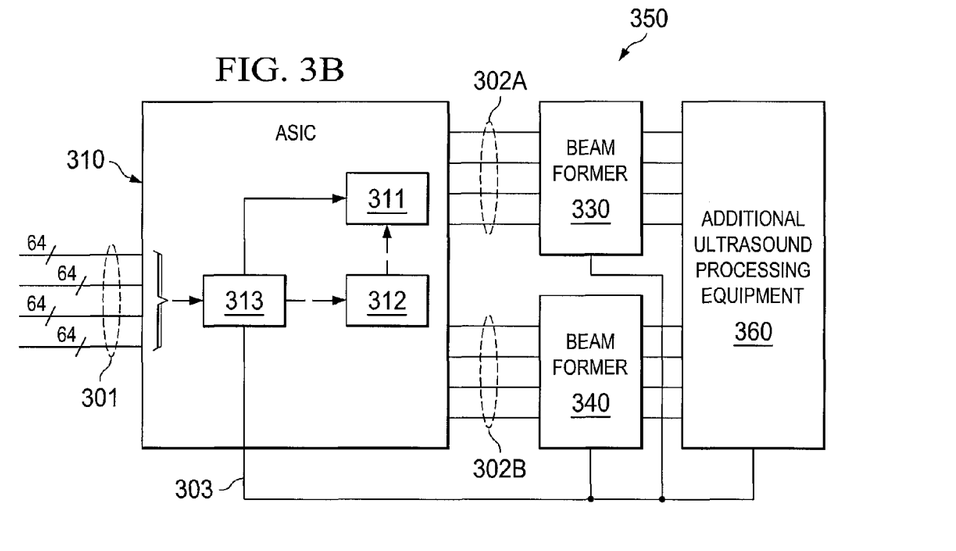
FIG. 3B is an illustration of an exemplary system, adapted according to various embodiments, employing an ASIC adapted for use in multiple system configurations and for performing cross-point switch operations.

FIG. 3B is an illustration of exemplary system 350, adapted according to various embodiments, employing ASIC 310 adapted for use in multiple system configurations and for performing cross-point switch operations. In the embodiment depicted in FIG. 3A, ASIC 310 is used to reduce a number of signal channels from a transducer to additional ultrasound processing equipment 420. In FIG. 3B, the same ASIC is used not to decrease a number of signal channels, but to define a number of receive signal channels for processing by a number of beam formers (often increasing a total number of receive channels), and therefore, to enhance a display. As explained earlier, imaging is usually accomplished in lines, and those lines may be arranged in a frame on a display to provide a picture recognizable by a human. In higher-power-consumption and higher-processing-power systems, a single transmit may be used to form several transmit and receive apertures, thereby allowing the system to gather data on multiple lines or on multiple points on a single line with a single transmit pulse. In this example, an aperture is a particular grouping of transducer elements that together form a "view" of a line, and one or more apertures may often overlap in the particular elements that they utilize. Since one transmit may be used to examine points on multiple lines, such systems may utilize a receive operation that gathers information for multiple lines at one time for a single transmit. Such an operation may be referred to as "multi-line."

In such systems, a transducer (not shown) may transmit, and then a receive operation may be accomplished, for example, as follows: The transducer may output signals representing reflections of sound waves on receive signal channels. Those receive signal channels may be received by an ASIC (not shown), such as ASIC 210, which reduces the number of receive signal channels by, for example, using muxes. Then those receive signal channels 301 are input into ASIC 310. In such embodiments, any number of signal channels may be input into ASIC 310, but in this example, it will be presumed that sixty-four signal channels are input into ASIC 310. ASIC 310 includes circuitry 311-313, similar to circuitry 311-313 in FIG. 3A, which is operable to provide cross-point switching functionality. Such cross point switch, in this example, is used to direct particular signal channels to multiple beam formers. A particular combination of receive signal channels sent to a beam former may represent one aperture, focusing on a particular line. In this embodiment, both beam formers 330 and 340 are connected by digital serial bus 303 to logic circuitry 313 in ASIC 310. Each beam former 330 and 340 instructs logic 313 to direct circuitry 311 to process the input data. Each beam former 330 and 340 sends instructions via bus 303 which signal channels to direct to which beam former 330 and 340. Accordingly, the cross point switch functionality of ASIC 310 allows ASIC 310 to route to each beam former 330 and 340 a number of receive signal channels (302A and 302B, respectively) representing an aperture.

Thus, for every transmit, a receive is being performed for multiple lines. If receives are done for two lines at a time, the frame rate may be doubled, allowing the system in this example embodiment to better display motion In this example embodiment, ASIC 310 inputs sixty-four signal channels and outputs any appropriate number of signal channels to each beam former to facilitate multi-line operations. Accordingly, in some embodiments, each beam former 330 and 340 may be responsible for an aperture defined by thirty-two signal channels. Accordingly, circuitry 311 is operable to output to each beam former information in thirty-two signal channels (receive channels 302A and 302B) defining an aperture. Two apertures may be defined by many of the same signal channels, such that each of receive channels 302A or 302B output to each beam former 330 or 340 may contain many of the same signal channels as the other set of thirty-two signal channels 302B or 302A. Further, sixty-four signal channels may be output to each beam former, such that each beam former views an aperture made up of the same signal channels as the other beam former; however, processing later may apply different delays and weights to the individual signal channels in each aperture, thereby defining different lines from the same signal channels. Any number of input and output receive signal channels is within the scope of the invention, and various embodiments may use an ASIC, such as ASIC 310, to provide as many signal channels from a transducer to one or more beam formers as needed. Additionally, any or all signal channels may be summed before being cross-point switched.

Accordingly, ASIC 310 may be used to decrease a number of signal channels from a transducer to one or more control/processing circuits, through, for example, symmetrical summing, as in FIG. 3A. Further, the same ASIC 310 may be used to increase a number of channels from a transducer to one or more control/processing circuits, through, for example, cross point switching, as in the example multi-line embodiment of FIG. 3B. Thus, ASIC 310 may be used for different functions by different systems. Because ASIC 310 may be used to define a wide range of signal channels, ASIC 310 may be useable in multiple system configurations. For example, ASIC 310 may be used in a lower-end or portable system to decrease a number of signal channels to limit the amount to processing power needed for such system and to make the system compatible with a higher-end transducer. Alternatively, ASIC 310 may also be used in higher-end or stand-alone systems to increase a number of signal channels to one or more control/processing circuits to facilitate such functions as multi-line. This modular property of ASIC 310 makes it ideal for some manufacturers, especially those manufacturers that may produce multiple models of an imaging platform, wherein some models may be lower-cost or portable models, and some models may be higher-cost, higher-end, or stand-alone models.

Figure 4:
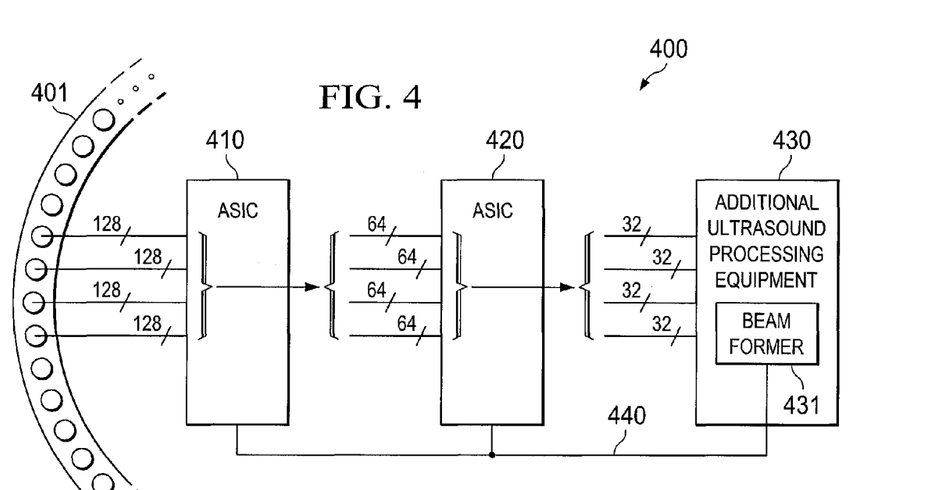
FIG. 4 is an illustration of an exemplary system, adapted according to various embodiments, employing multiple ASICs, those ASICs each adapted for use in a variety of systems utilizing different numbers of channels.

FIG. 4 is an illustration of an exemplary system 400, adapted according to various embodiments, employing multiple ASICs, those ASICs each adapted for use in a variety of systems utilizing different numbers of signal channels. During a receive operation, transducer 401 converts reflections of ultrasonic waves into electrical signals, which it feeds to ASIC 410, in this example, via one hundred twenty-eight signal channels. In this example, ASIC 410 is similar to ASIC 210 of FIGS. 2A and 2B, in that it reduces a number of receive signal channels. During both receive and transmit operations, the components in ASIC 410 are controlled by beam former 431 via digital bus 440, such as, for example, by stimulating enable and select lines to form beams and to receive reflections. In this example, ASIC 410 acts as a bank of 2:1 muxes, but in alternate configurations, each of the 2:1 muxes may be paired to form one 4:1 mux by utilizing the enable lines on each mux to select an output from one mux of each pair.

Sixty-four receive signal channels are then input into ASIC 420, which in this example, is similar to ASIC 310 of FIGS. 3A and 3B. ASIC 420 may sum the signal channels, may act as a cross point switch, or may do both. In this example, such functionality is dictated by the architecture of system 400, such that if system 400 is an imaging system that performs multi-line operations, ASIC 420 will act as a cross-point switch. If system 400 is an imaging system that utilizes only thirty-two receive channels by additional ultrasound equipment 430, then the architecture may dictate that ASIC 420 act as a summer to reduce sixty-four signal channels to thirty-two summed pairs through use of a summing operation. Such summing operations and cross-point switch operations are controlled, in this example, by beam former 431, which communicates to the components in ASIC 420 via digital bus 440. Such control may be similar to the operations discussed with regard to FIGS. 3A and 3B. Thus, as illustrated in FIG. 4, multiple ASICs may be used in a single system to provide desired functionality.

Figure 5:
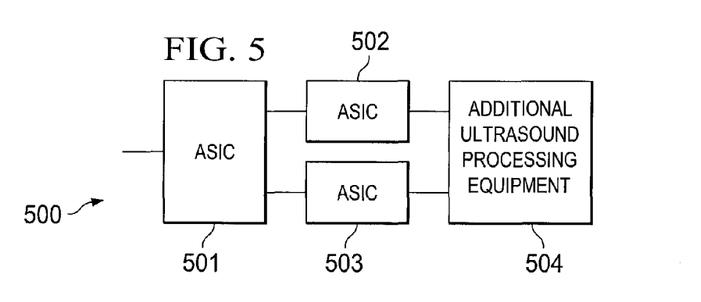
FIG. 5 is an illustration of an exemplary system, adapted according to various embodiments, employing multiple ASICs for use in multiple system configurations.

FIG. 5 is an illustration of exemplary system 500, adapted according to various embodiments, employing multiple ASICs for use in multiple system configurations. Specifically, system 500 employs ASICs 501-503, which, in turn, output channels to additional ultrasound processing equipment 504. In this example embodiment, ASIC 501 may be similar to ASICs 210 and 310. System 500 may be utilized, for example, in an embodiment for performing multi-line, such that ASICs 501-503 may be used to increase a number of signal channels from a transducer to one or more beam formers. This figure illustrates that the operability of ASICs to define a number of signal channels from a transducer to one or more control circuits may be extended by implementing a number of ASICs, such as ASICs 502 and 503, to further increase or decrease the number of signal channels available for analysis in a system. Thus, another modular aspect of these ASICs, such as ASICs 210 and 310 of FIGS. 2A-3B, is that multiple of those ASICs may be utilized to create a system with as few or as many signal channels and as much as or as little processing power as a manufacturer wishes to implement in a system. Thus, a modular platform may be created which utilizes a standard chip set, but which may be used to build multiple systems.

Figure 6:
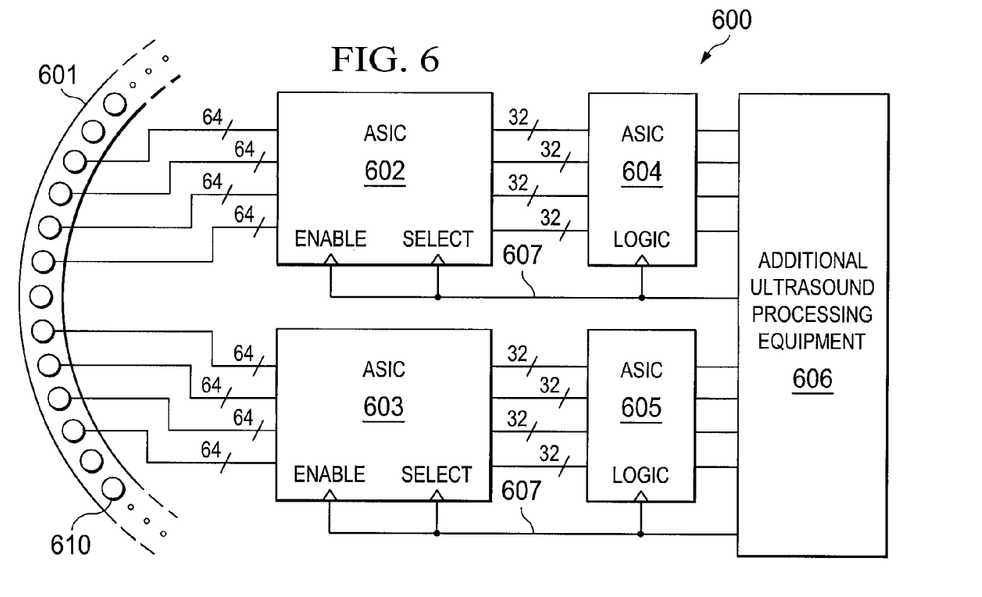
FIG. 6 is an illustration of an example system, adapted according to various embodiments, employing multiple ASICS for use in multiple system configurations.

FIG. 6 is an illustration of example system 600, adapted according to various embodiments, employing multiple ASICS for use in multiple system configurations. Specifically, FIG. 6 is a schematic diagram of a portion of a diagnostic sonogram machine according to various embodiments. System 600 includes transducer 601, which utilizes a number of transducer elements 610, represented as circles within transducer 601. System 600 also includes transmission ASICs 602 and 603 (similar to ASIC 210 of FIGS. 2A and 2B), receiving ASICs 604 and 605 (similar to ASIC 310 of FIGS. 3A and 3B), and additional ultrasound processing equipment 606. Additional ultrasound processing equipment 606 may include a variety of components, such as one or more beam formers (not shown), a Digital Signal Processor (DSP, not shown) and digital scan converter for processing an image, and a display for presenting to a user the image. Transmission ASICs 602 and 603 operate to supply transducer 601 with high-power pulses (amplified pulses from one or more beam formers) to produce an acoustic beam for use in diagnostic sonography and operates to reduce a number of receive and transmit channels for transducer 601. Receiving ASICs 604 and 605 operate to receive signals from transducer 601 through transmission ASICs 602 and 603, respectively, and operate to determine a number of receive signal channels to one or more beam formers included in additional ultrasound processing equipment 606. Beam formers act to provide control signals to transducer 601 and ASICs 602-605 (as explained above), and to create acoustic beams, thereby facilitating the operation of the sonogram machine.

this example embodiment, transducer 601 includes one hundred twenty-eight transducer elements, which are divided into two sets of sixty-four, with each element in communication with one of ASICs 602 or 603. On the transmit side, ASICs 602 and 603 each input thirty-two transmit signal channels, which are split and amplified by amplifiers with enable switches, as in FIGS. 2A and 2B. The transmit signal channels are routed from one or more beam formers in additional ultrasound processing equipment 606, which operate to control the beams produced by transducer 601. The enable switches on the amplifiers on the transmission signal channels are controlled by the one or more beam formers in additional ultrasound processing equipment 606, as discussed with regard to FIGS. 2A and 2B, via digital serial bus 607. On the receive side, each ASIC 601 and 602 inputs sixty-four signal channels and outputs thirty-two signal channels, by, for example, the use of muxes, as described with regard to FIGS. 2A and 2B. In this example, the muxes are used as 2:1 muxes, but in alternate embodiments could be used as 4:1 muxes by paring up two muxes and using enable switches on each to select one of every two. The muxes are controlled by signals to select switches from one or more beam formers in additional ultrasound processing equipment 606, via bus 607. In some embodiments in which enable switches on each of the muxes are used, those enable switches are also controlled by one or more beam formers, via bus 607. The 2:1 muxes reduce the number of receive signal channels to thirty-two. It should be noted that there is no rule that the number of transmit signal channels be equal to the number of receive signal channels, as alternate embodiments may employ any appropriate number of transmit and receive signal channels.

ASICs 604 and 605 then input thirty-two receive signal channels each. Logic inside each ASIC 604 and 605 is controlled, in this example embodiment, by one or more beam formers, via bus 607. The logic inside each ASIC 604 and 605 may direct that data be processed in a summing operation, or in a cross-point switch operation, or both. The number of receive signal channels output to additional ultrasound processing equipment 606 may depend on whether the system requires a summing operation or whether the system performs a multi-line technique, as discussed above. Either way, the receive signal channels from each ASIC 604 and 605, in this example, are fed to one or more beam formers so that the beam formers may analyze the data and produce subsequent beams through controlling the other components in response to the data, and then the data is sent to other components in additional ultrasound processing equipment 606, such as digital scan converter to process receive signals into an image, and a monitor to display the image.

While the example embodiments of FIGS. 1-6 utilized one, two, thirty-two, or sixty-four signal channels, those numbers are merely illustrative, as any number of signal channels are within the scope of the invention. Further, while the embodiments of FIGS. 1-6 employed separate ASICs for transmit and receive operability, it should be noted that such operability may be placed on a single ASIC, or that operability may be further segregated among ASICs. Any division of operability and any number of ASICs employing transmit or receive functionality are within the scope of the invention.

Figure 7:
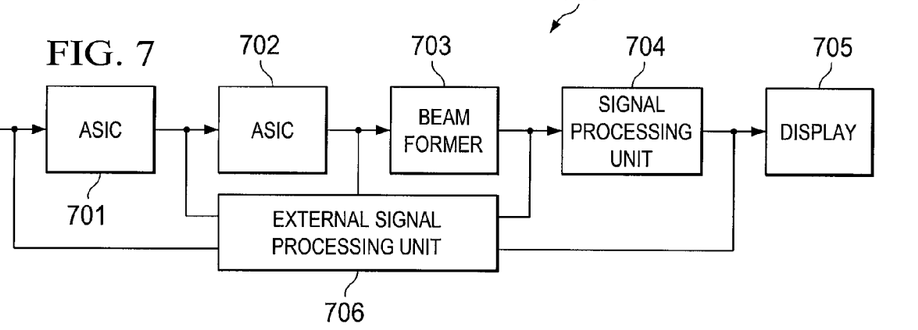
FIG. 7 is a block diagram of exemplary system 700, adapted according to various embodiments, employing ASICs for use in multiple systems and employing a signal processing unit, such as a DSP or a FPGA, for improved functionality.

FIG. 7 is a block diagram of exemplary system 700, adapted according to various embodiments, employing ASICs for use in multiple systems and employing a signal processing unit, such as a DSP or a FPGA, for improved functionality. System 700, in this example, is a system similar to systems 100-600 of FIGS. 1-6, in that it employs ASICs adapted for use in variety of systems having different numbers of signal channels. System 700 includes ASICs 701-702, beam former 703, signal processing unit 704, display 705, and additional, external signal processing unit 706. Similar practical systems may employ many more components or may omit one or more components of system 700. The makeup of system 700 is exemplary, and as such, any number ASICs and other components is within the scope of embodiments. System 700 may be, for example, for use in a diagnostic sonogram system, such that information from a transducer (not shown) may be passed along a data path through ASICs 701 and 702, which may define a number of signal channels for use in system 700, beam former 703, which may operate to control the transmitting and receiving of system 700, signal processing unit 704 (which may contain a DSP and/or a digital scan converter), which may operate to create a human-viewable image out of the information it receives by adding Color Power Doppler (CPD) and Tissue Harmonic Imaging (THI), and display 705 for displaying the image to a user. In this embodiment, external signal processing unit 706 has been added and includes connections at various points along the data path, but is not directly in the data path—thus, it is "external" to the data path. External signal processing unit 706 may capture data along the data path and may also insert data along that data path. In this example, external signal processing unit 706 is programmable and may operate to provide upgradeability to system 700 by receiving programming to add new modes of operation to system 700. For example, a system which employs a signal processing unit, such as external signal processing unit 706, may utilize the signal processing unit to add, for example, Pulse Wave Doppler (PWD) or Color Velocity Doppler (CVD) functionality even if the system originally did not support such functionality.

The upgradeability of system 700 may be useful in higher-end systems wherein the cost and power consumption of external signal processing unit 706 is less of a factor than in lower-end and portable systems. The option to add a signal processing unit, such as external signal processing unit 706, to a system may allow a manufacturer to offer in some higher-end systems the ability to keep up with advancements in the technology without requiring all new ASICs. The upgradeability offered to this system by external signal processing unit 706 may provide much flexibility to a manufacturer of such a system, especially when used in combination with the modularity of ASICs, such as ASICs 701 and 702. Such modularity and upgradeability of systems may allow a manufacturer to offer to wide variety of systems to customers, wherein those systems utilize many of the same chip sets and may be quite similar in internal structure and manufacturing techniques.

Systems 100-700 of FIGS. 1-7 are exemplary, and are not exclusive. Accordingly, features from any of systems 100-700 may be combined with features from other systems, including features not mentioned in FIGS. 1-7. Further, other systems, while within the scope of the invention, may omit some features from those example embodiments.

Figure 8:
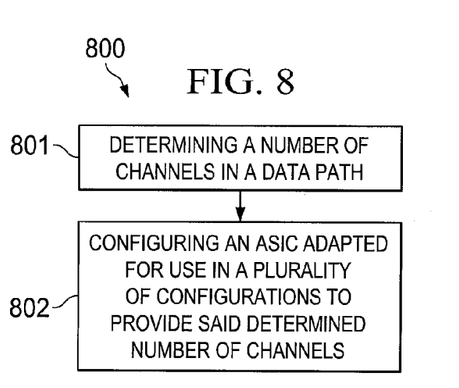
FIG. 8 is a block diagram illustrating an exemplary method, adapted according to various embodiments, for designing a system that employs ASICs for use in multiple systems.

FIG. 8 is a block diagram illustrating exemplary method 800, adapted according to various embodiments, for designing a system that employs ASICs for use in multiple systems. In block 801, a number of signal channels for use in a data path are determined. In block 802, an ASIC adapted for use in a plurality of configurations is configured to provide the determined number of signal channels. Such method may be useful, for example, in the design and manufacture of diagnostic systems, such as sonogram systems. By using the method, multiple systems may be created, from higher-power-consumption, higher-processing-power systems end to lower-power-consumption, lower-processing-power systems, utilizing similar chip sets.

Figure 9:
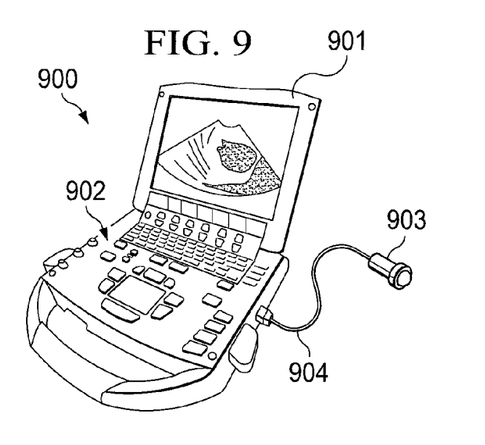
FIG. 9 is an illustration of an exemplary sonogram imaging system adapted according to various embodiments.

FIG. 9 is an illustration of exemplary sonogram imaging system 900 adapted according to various embodiments. System 900 includes, among other things, display 901, operable to display to a user an image produced by interpreting reflections of sound waves, as described earlier. Display 901, in this example embodiment, is also capable of functioning as a user interface device, thereby allowing a user to interact with a graphical user interface employed by system 900. Thus, display 901 may act as a computer monitor, allowing a user to view movement of a cursor and to view his or her interaction with the various available functions, possibly represented by icons on display 901. System 900 also includes user interface 902, which allows a user to enter information to system 900 and to interact therewith. User interface 902 may comprise a keyboard, a panel of buttons, a touchpad, and/or any other kind of device operable to receive input from a user. Transducer 903 is included in system 900, and is operable to transmit and receive sound waves for sonographic analysis. Transducer 903 may be a transducer array, as described above, enclosed in a housing and able to be held in a hand of a healthcare worker as a sonogram is being performed. Transducer 903 is connected to circuitry within system 903 by cord 904, which in this example embodiment includes processors, ASICs, beam formers, and other components to support the functionality of system 900. System 900 is compatible with the example embodiments depicted in FIGS. 1-8, such that the systems and methods described herein may be included in system 900. System 900 may also include features not described in the above embodiments, while it remains within the scope of the invention.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A system comprising:
   an application specific integrated circuit (ASIC) comprising:
      a plurality of components for providing a first level of signal channel reduction and a second level of signal channel reduction, wherein said first and second levels of signal channel reduction are achieved by selecting which of said components to enable; and
      a plurality of multiplexers providing N to M signal multiplexing,
         wherein in the first level of signal channel reduction said ASIC is configured to provide N to M signal multiplexing;
         wherein in the second level of signal channel reduction said ASIC is configured to provide N to M/2 signal multiplexing;
         wherein said plurality of multiplexers include N signal inputs, M signal outputs, at least one select signal input, and at least one enable signal input, said enable signal input being utilized in providing said N to M/2 signal multiplexing in said second level of signal channel reduction; and
         wherein said plurality of multiplexers are divided into hardwired pairs, and only one of each pair is enabled during a receive operation.

2. The system of claim 1, wherein at least one of said select signal input and said enable signal input comprise a digital serial control bus.

3. The system of claim 1, wherein said ASIC comprises:
   a circuit configurable to provide a cross-point switch function in the first level of signal channel reduction and to provide a signal summer function in the second level of signal channel reduction.

4. The system of claim 3, wherein said cross-point switch function comprises selectively routing signal channels to one or more beam formers.

5. The system of claim 3, wherein the signal summer function comprises a symmetric signal summing operation.

6. The system of claim 5, wherein the symmetric signal summing operation comprises summing one or more signals that are determined to be of similar weight and delay.

7. A method for using an ASIC that provides a first level of signal channel reduction and a second level of signal channel reduction, the method comprising:
   determining a number of signal channels for use in a data path;
   configuring the ASIC to provide the determined number of signal channels by selecting one or more components in the ASIC to provide the first or second level of signal channel reduction; and
   summing data on each of at least two channels by the ASIC, wherein summing data comprises: receiving signals from a control circuit instructing that certain of the channels are to be divided into symmetric pairs and those pairs added, thereby decreasing the number of output channels; and routing the added pairs to one or more beam formers.

8. The method of claim 7 further comprising operating circuitry on the ASIC as a plurality of multiplexers, thereby decreasing the number of channels from a transducer array to a beam former.

9. The method of claim 8, wherein the multiplexers are 2:1 multiplexers, and wherein operating as a plurality of multiplexers comprises selectively enabling one of every two 2:1 multiplexers, thereby providing 4:1 multiplexing functionality.

10. The method of claim 9, wherein selectively enabling comprises stimulating an enable switch on one of every two 2:1 multiplexers by a control signal from a beam former.

11. The method of claim 7 further comprising:
   implementing in a sonogram imaging system the ASIC, the one or more beam formers, the data path, and a transducer array, wherein the ASIC, the one or more beam formers, and the transducer array are in communication with the data path.

12. A method for using an ASIC that provides a first level of signal channel reduction and a second level of signal channel reduction, the method comprising:
   determining a number of signal channels for use in a data path;
   configuring the ASIC to provide the determined number of signal channels by selecting one or more components in the ASIC to provide the first or second level of signal channel reduction; and
   summing data on each of at least two channels by the ASIC, wherein summing data comprises: receiving signals from a control circuit instructing that certain of the channels are to be divided into adjacent pairs and those pairs added, thereby decreasing the number of output channels; and routing the added pairs to one or more beam formers.

13. The method of claim 12 further comprising:
   implementing in a sonogram imaging system the ASIC, the one or more beam formers, the data path, and a transducer array, wherein the ASIC, the one or more beam formers, and the transducer array are in communication with the data path.

14. The method of claim 12 further comprising:
   operating circuitry on the ASIC as a plurality of multiplexers, thereby decreasing the number of channels from a transducer array to the one or more beam formers.

15. The method of claim 14, wherein the multiplexers are 2:1 multiplexers, and wherein operating as a plurality of multiplexers comprises selectively enabling one of every two 2:1 multiplexers, thereby providing 4:1 multiplexing functionality.

16. The method of claim 15, wherein selectively enabling comprises stimulating an enable switch on one of every two 2:1 multiplexers by a control signal from the one or more beam formers.

17. A method for using an ASIC that provides a first level of signal channel reduction and a second level of signal channel reduction, the method comprising:
- determining a number of signal channels for use in a data path;
- configuring the ASIC to provide the determined number of signal channels by selecting one or more components in the ASIC to provide the first or second level of signal channel reduction;
- implementing two beam formers in communication with the data path; and
- operating the two beam formers and a transducer array to form multiple receive beams.

18. The method of claim 17 further comprising operating the two beam formers and the transducer array perform a multi-line receive operation.

19. A method for using an ASIC that provides a first level of signal channel reduction and a second level of signal channel reduction, the method comprising:
- determining a number of signal channels for use in a data path;
- configuring the ASIC to provide the determined number of signal channels by selecting one or more components in the ASIC to provide the first or second level of signal channel reduction;
- implementing a signal processing unit to communicate with the data path at a number of points;
- programming the signal processing unit with code to provide a mode of functionality not originally included in a platform using the method; and
- operating the signal processing unit to intercept and insert data along the number of points on the path, thereby instructing the platform to perform the mode.

* * * * *